United States Patent
Keyes et al.

(10) Patent No.: US 10,959,784 B2
(45) Date of Patent: Mar. 30, 2021

(54) DETERMINING BALLOON CATHETER CONTACT WITH ANATOMY USING ULTRASOUND

(71) Applicant: Biosense Webster (Israel) Ltd., Yokneam (IL)

(72) Inventors: Joseph Thomas Keyes, Glendora, CA (US); Maribeth Wilczynski, Glendale, CA (US); Assaf Govari, Haifa (IL); Andres Altmann, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 286 days.

(21) Appl. No.: 15/792,404

(22) Filed: Oct. 24, 2017

(65) Prior Publication Data

US 2019/0117315 A1  Apr. 25, 2019

(51) Int. Cl.
*A61B 34/20* (2016.01)
*A61B 18/14* (2006.01)
(Continued)

(52) U.S. Cl.
CPC ............ *A61B 34/20* (2016.02); *A61B 5/0408* (2013.01); *A61B 8/0841* (2013.01); *A61B 8/0883* (2013.01); *A61B 8/12* (2013.01); *A61B 8/445* (2013.01); *A61B 8/4477* (2013.01); *A61B 8/4494* (2013.01); *A61B 8/461* (2013.01);
(Continued)

(58) Field of Classification Search
CPC ............ A61B 34/20; A61B 2034/2063; A61B 2034/2051; A61B 5/042; A61B 5/063; A61B 18/1492; A61B 2018/0022; A61B 2018/00351; A61B 2018/00577; A61B 8/12; A61B 8/4245; A61B 8/4254; A61B 8/44

See application file for complete search history.

(56) References Cited

U.S. PATENT DOCUMENTS 5,190,046 A  3/1993  Shturman
5,588,432 A  12/1996  Crowley
(Continued)

FOREIGN PATENT DOCUMENTS

WO  WO 2016/183285 A1  11/2016

OTHER PUBLICATIONS

International Search Report dated Jan. 7, 2019, International Application No. PCT/US2018/055134.

*Primary Examiner* — Carolyn A Pehlke (57) ABSTRACT

A medical system includes a shaft, an inflatable balloon, a radial array of ultrasound transducers and a processor. The shaft is configured for insertion into a body of a patient. The inflatable balloon is coupled to a distal end of the shaft and configured to perform a treatment to surrounding anatomy. The ultrasound transducers are distributed circumferentially around the distal end of the shaft inside the balloon, and configured to transmit ultrasound waves at respective radial directions and receive respective ultrasound reflections. The processor is configured to estimate and output to a user, based on the ultrasound reflections received from the ultrasound transducers, an extent of mechanical contact between the balloon and the surrounding anatomy.

18 Claims, 4 Drawing Sheets

(51) Int. Cl.

| | | |
|---|---|---|
| *A61B 8/00* | (2006.01) | |
| *A61B 8/12* | (2006.01) | |
| *A61B 8/08* | (2006.01) | |
| *A61B 5/0408* | (2006.01) | |
| *A61B 17/34* | (2006.01) | |
| *A61B 18/00* | (2006.01) | |
| *A61B 18/02* | (2006.01) | |
| *A61B 18/18* | (2006.01) | |
| *A61B 90/00* | (2016.01) | |
| *A61B 17/22* | (2006.01) | |
| *A61B 17/24* | (2006.01) | |
| *A61B 17/00* | (2006.01) | |
| *G06T 7/00* | (2017.01) | |

(52) U.S. Cl.
CPC ........ *A61B 8/5223* (2013.01); *A61B 18/1492* (2013.01); *A61B 2017/00106* (2013.01); *A61B 2017/22001* (2013.01); *A61B 2017/22097* (2013.01); *A61B 2017/242* (2013.01); *A61B 2017/3413* (2013.01); *A61B 2018/0022* (2013.01); *A61B 2018/00375* (2013.01); *A61B 2018/00577* (2013.01); *A61B 2018/00613* (2013.01); *A61B 2018/0212* (2013.01); *A61B 2018/1467* (2013.01); *A61B 2018/1861* (2013.01); *A61B 2034/2063* (2016.02); *A61B 2090/061* (2016.02); *A61B 2090/065* (2016.02); *A61B 2090/3784* (2016.02); *G06T 7/0012* (2013.01)

(56) References Cited

U.S. PATENT DOCUMENTS

| | | |
|---|---|---|
| 6,117,101 A | 9/2000 | Diederich et al. |
| 6,547,788 B1 * | 4/2003 | Maguire ................ A61B 18/00 606/41 |
| 2002/0068885 A1 | 6/2002 | Harhen et al. |
| 2003/0105509 A1 | 6/2003 | Jang et al. |
| 2003/0208119 A1 | 11/2003 | Crowley |
| 2014/0081301 A1 | 3/2014 | Tran et al. |
| 2015/0257732 A1 | 9/2015 | Ryan |
| 2016/0051321 A1 | 2/2016 | Salahieh et al. |

* cited by examiner

DETERMINING BALLOON CATHETER CONTACT WITH ANATOMY USING ULTRASOUND

FIELD OF THE INVENTION

The present invention relates generally to invasive medical instruments, and particularly to intra-body medical probes employing ultrasound.

BACKGROUND OF THE INVENTION

Invasive ultrasound techniques have been used to assess an anatomy within the body. For example, U.S. Patent Application Publication 2003/0208119 describes a medical device for creating images of tissue within a body. The device includes a shaft which carries an imaging device such as a rotating ultrasound transducer. The device optionally includes an inflatable balloon.

As another example, U.S. Pat. No. 5,588,432 describes an acoustic imaging system for use within a heart comprising a catheter, an ultrasound device incorporated into the catheter, and an electrode mounted on the catheter. The ultrasound device directs ultrasonic signals toward an internal structure in the heart to create an ultrasonic image, and the electrode is arranged for electrical contact with the internal structure. An acoustic marker mounted on the catheter emits a sonic wave when electrically excited. A central processing unit creates a graphical representation of the internal structure, and super-imposes items of data onto the graphical representation at locations that represent the respective plurality of locations within the internal structure corresponding to the plurality of items of data. A display system displays the graphical representation onto which the plurality of items of data are super-imposed.

U.S. Pat. No. 5,190,046 describes an ultrasound imaging balloon catheter for imaging near a wall of a cavity or passageway. The apparatus includes an elongated catheter having a primary lumen with a distal opening enveloped by the balloon. A pre-shaped ultrasound catheter carrying ultrasound transducer elements can be advanced through the catheter and inserted into the inflated balloon. The shape of the distal portion of the ultrasound catheter positions the ultrasound transducer elements radially outwardly of the catheter lumen, and preferably adjacent to the wall of the balloon, thus centering the image close to the wall of the cavity or passageway, giving greater depth of image at the portion of the wall of interest.

U.S. Patent Application Publication 2003/0105509 describes a catheter system comprising a balloon angioplasty device disposed about a common lumen near its distal end. The balloon catheter is pre-fitted with a stent which is deployed when the balloon is inflated. The common lumen is in communication with multiple lumens within a proximal region of the catheter body to allow for positioning of the catheter over a movable guide wire and convenient delivery of imaging or interventional devices to a desired region of a body passageway being treated. The procedure for stent deployment optionally includes steps of imaging a lumen by ultrasound before and after stent deployment to identify the site at which a stent is needed, to confirm that the stent is being and has been deployed at a longitudinal position which does not overlap a branched segment of the body passageway, and to ensure that the stent has been radially opened to an optimum diameter.

SUMMARY OF THE INVENTION

An embodiment of the present invention provides a medical system including a shaft, an inflatable balloon, a radial array of ultrasound transducers and a processor. The shaft is configured for insertion into a body of a patient. The inflatable balloon is coupled to a distal end of the shaft and configured to perform a treatment to surrounding anatomy. The ultrasound transducers are distributed circumferentially around the distal end of the shaft inside the balloon, and configured to transmit ultrasound waves at respective radial directions and receive respective ultrasound reflections. The processor is configured to estimate and output to a user, based on the ultrasound reflections received from the ultrasound transducers, an extent of mechanical contact between the balloon and the surrounding anatomy.

In some embodiments, the inflatable balloon is configured to perform at least one of RF ablation, microwave ablation, irreversible electroporation, cryo-ablation, angioplasty, valvuloplasty and pulmonary dilation treatment.

In some embodiments, the radial array of ultrasound transducers is configured to transmit the ultrasound waves at respective radial directions and receive the respective ultrasound reflections at the respective radial directions that cover an entire circumference of the inflatable balloon.

In some embodiments, the one or more of the radial directions point to RF ablation electrodes disposed on the inflatable balloon.

In an embodiment, the processor is configured to calculate, based on the ultrasound reflections, respective radial distances between multiple locations on the inflatable balloon and multiple respective sites on a surface of the surrounding anatomy, and to estimate the extent of mechanical contact between the balloon and the surface of the surrounding anatomy based on the radial distances.

In another embodiment, the processor is configured to calculate the radial distances by analyzing respective one-dimensional echo-profiles, comprising peaks indicative of the respective radial distances.

In some embodiments, each of the ultrasound transducers is configured to produce a respective one-dimensional echo profile at a respective radial direction.

In an embodiment, the processor is configured to analyze each echo profile along the respective radial direction independently of other echo profiles.

In another embodiment, the processor is configured to present the radial distances graphically to the user.

In an embodiment, the processor is configured to update the displayed radial distances at a given rate or by request.

There is additionally provided, in accordance with an embodiment of the present invention, a method including inserting into a body of a patient an inflatable balloon coupled to a distal end of a shaft, for performing a treatment to surrounding anatomy. Ultrasound waves are transmitted at respective radial directions, and respective ultrasound reflections are received, using a radial array of ultrasound transducers, which are distributed circumferentially around the distal end of the shaft inside the balloon. An extent of mechanical contact between the balloon and the surrounding anatomy is estimated and outputted to a user, based on the ultrasound reflections received from the ultrasound transducers.

The present invention will be more fully understood from the following detailed description of the embodiments thereof, taken together with the drawings in which:

DETAILED DESCRIPTION OF EMBODIMENTS

Overview

Some cardiac ablation procedures are performed using an inflatable balloon having ablation electrodes thereon. Such procedures require in general that the inflatable balloon will be positioned in full contact with the surface of target surrounding anatomy. Full contact means continuous contact between the inflatable balloon wall and the target surrounding anatomy surface, which extends around an entire circumference of the balloon.

Embodiments of the present invention that are described herein provide an ultrasound-based invasive medical instrument, as well as methods of ultrasound data analysis and visualization, which enable the treating physician to verify that the saline-inflated balloon wall is indeed in full contact with the surface of the surrounding anatomy to be treated, both before and during the treatment.

In some embodiments, the distal end of the medical instrument, e.g., a catheter, comprises a shaft, and an inflatable balloon having ablation electrodes coupled to the distal end of the shaft. An array of multiple ultrasound transducers is distributed radially around the axis of the shaft, in the interior of the balloon.

During positioning of the balloon, for example within a left atrium of a heart, the balloon wall will initially come only partially in contact with the surrounding anatomy surface (i.e., with respect to a target of achieving contact between the balloon and tissue over a full circumference of the balloon). In embodiments of the disclosed invention, the balloon wall proximity to a surrounding anatomy is characterized by repeated measurements performed by the multiple-transducer ultrasound probe, taken at multiple respective radial directions around the balloon.

In some embodiments, a processor is configured to receive sets of such measurements and calculate from the measurements a set of respective radial distances between a respective set of locations distributed over the balloon wall and multiple respective sites distributed over the surface of the surrounding anatomy.

In an embodiment, a set of such radial distances distributed around a given circumference of the balloon is graphically presented to the physician on a monitor. The presentation may comprise a cross-sectional diagram illustrating the balloon circumference relative to the surrounding anatomy, with the radial distances presented as well to quantify the diagram. The physician navigating the balloon may have the diagram updated at a given refresh rate and/or may command an update of the diagram. Alternatively or additionally, the set of radial distances may be provided on the monitor in any other updatable format. In an optional embodiment, a percentage of circumferential contact is graphically presented to the physician on a monitor, where hundred percent (100%) means the entire saline-inflated balloon circumference is in contact with the anatomy.

The disclosed technique provides the physician a tool to assist him in navigating the inflatable balloon and positioning the balloon with a high degree of confidence that the balloon is in full contact with the target anatomy of the patient. Thus, the disclosed technique has distinct added value by improving the safety and efficacy of balloon catheter treatments.

Moreover, the disclosed techniques are typically fast and require only modest computational complexity. For example, each ultrasound transducer produces only a one-dimensional echo profile at a particular radial direction. The processor typically analyzes each echo profile separately, in order to calculate the distance between the balloon wall and the tissue at that radial direction.

System Description

Figure 1:
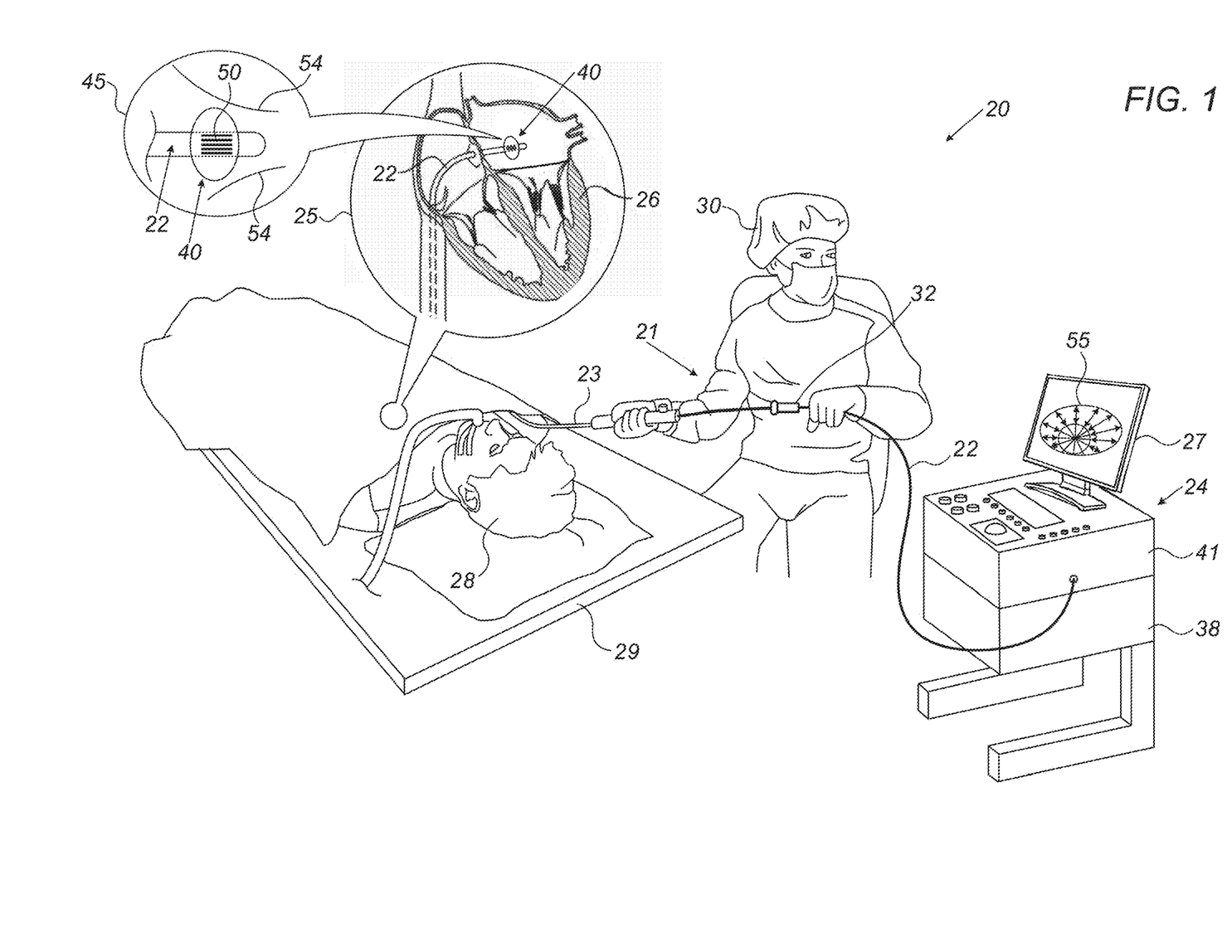
FIG. 1 is a schematic, pictorial illustration of a catheter-based ablation system comprising an inflatable balloon and an ultrasound probe, in accordance with an embodiment of the present invention.

FIG. 1 is a schematic, pictorial illustration of a catheter-based ablation system 20 comprising an inflatable balloon 40 and an ultrasound-probe 50, in accordance with an embodiment of the present invention. System 20 comprises a catheter 21, wherein a distal end of shaft 22 of the catheter is inserted through a sheath 23 into a heart 26 of a patient 28 lying on a table 29. The proximal end of catheter 21 is connected to a control console 24. In the embodiment described herein, catheter 21 may be used for any suitable therapeutic and/or diagnostic purposes, such as electrical sensing and/or ablation of tissue in heart 26.

Physician 30 navigates the distal end of shaft 22 to a target location in heart 26 by manipulating shaft 22 using a manipulator 32 near the proximal end of the catheter and/or deflection from the sheath 23. During the insertion of shaft 22, balloon 40 is maintained in a collapsed configuration by sheath 23. By containing balloon 40 in a collapsed configuration, sheath 23 also serves to minimize vascular trauma along the way to target location.

In an embodiment, inflatable balloon 40 shown in an inset 25 is configured to perform treatments such as RF ablation, cryo-ablation, angioplasty, valvuloplasty, pulmonary dilation, microwave ablation, and/or irreversible electroporation at a target location of heart 26. An inset 45 shows inflatable balloon 40 navigated to an ostium 54 of a pulmonary vein. As seen in inset 45, shaft distal end 22 contains ultrasound probe 50 inside balloon 40. Ultrasound Probe 50 comprises an array of multiple ultrasound transducers 52, which are distributed circumferentially around the shaft distal end at the shaft distal end (seen in FIG. 3A below).

Control console 24 comprises a processor 41, typically a general-purpose computer, with suitable front end and interface circuits 38 for receiving signals from catheter 21, as well as for applying treatment via catheter 21 in heart 26 and for controlling the other components of system 20.

Figure 3A:
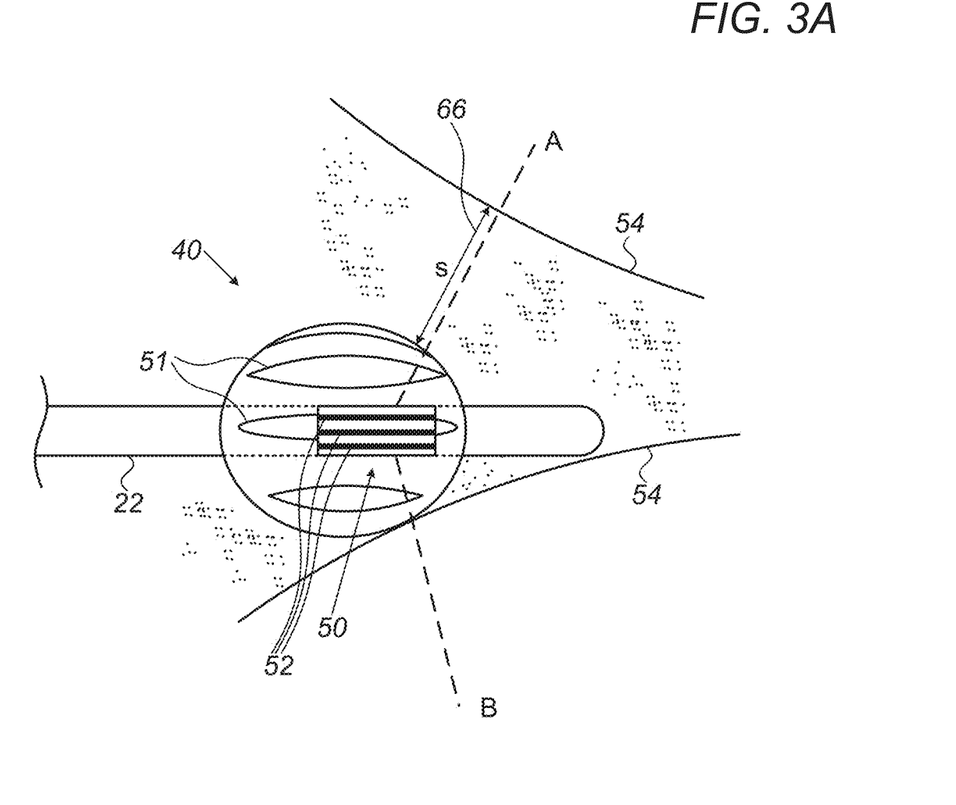
FIGS. 3A and 3B are schematic, pictorial illustrations of a Radio Frequency (RF) ablation inflatable balloon wall in partial contact with an ostium of a pulmonary vein, in accordance with an embodiment of the present invention.
Figure 3B:
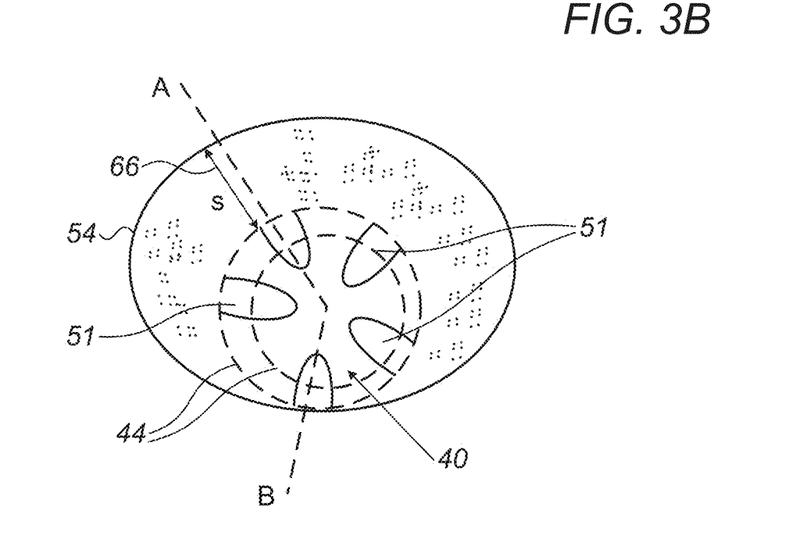
Figure 4:
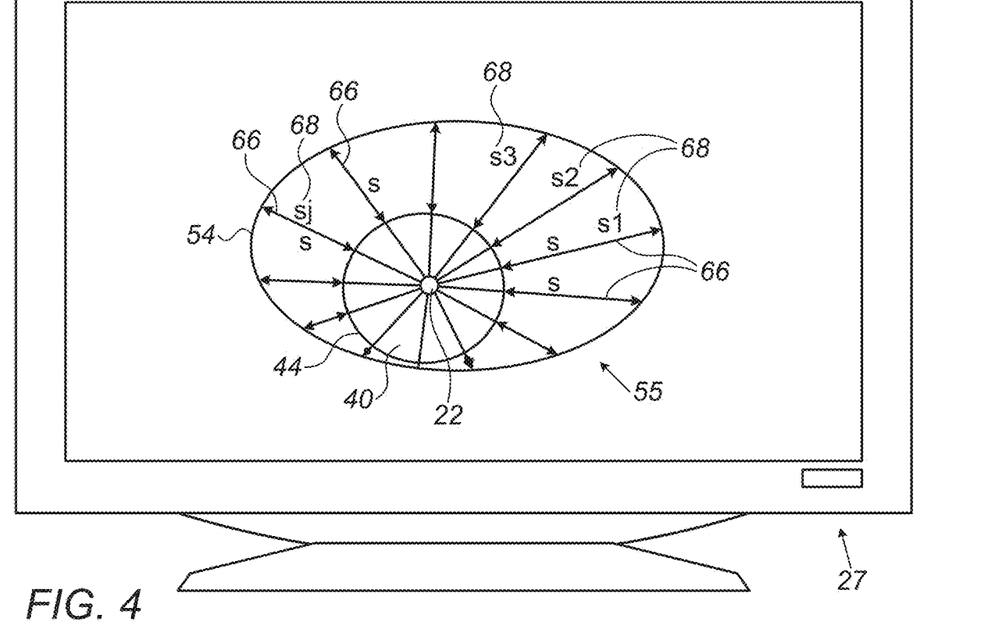
FIG. 4 is a schematic, pictorial illustration of a diagram of radial distances between an inflatable balloon wall and an ostium of a pulmonary vein, displayed to the physician on a monitor, in accordance with an embodiment of the present invention.

In some embodiments, processor 41 may be configured to receive multiple measurements from ultrasound transducers 52 and calculate from these measurements the extent to which balloon 40 wall is in contact with surrounding ostium 54 anatomy around an entire circumference of balloon 40 (examples of circumferences are seen in FIGS. 3B and 4). In an embodiment, the extent of balloon 40 wall proximity to a surrounding anatomy over an entire circumference of balloon 40 is presented to physician 30 on a monitor 27, e.g., in a graphical form of a diagram 55.

Processor 41 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise other components and perform non-cardiac catheterization treatments.

Determining Balloon Catheter Contact with Anatomy Using Ultrasound

Figure 2A:
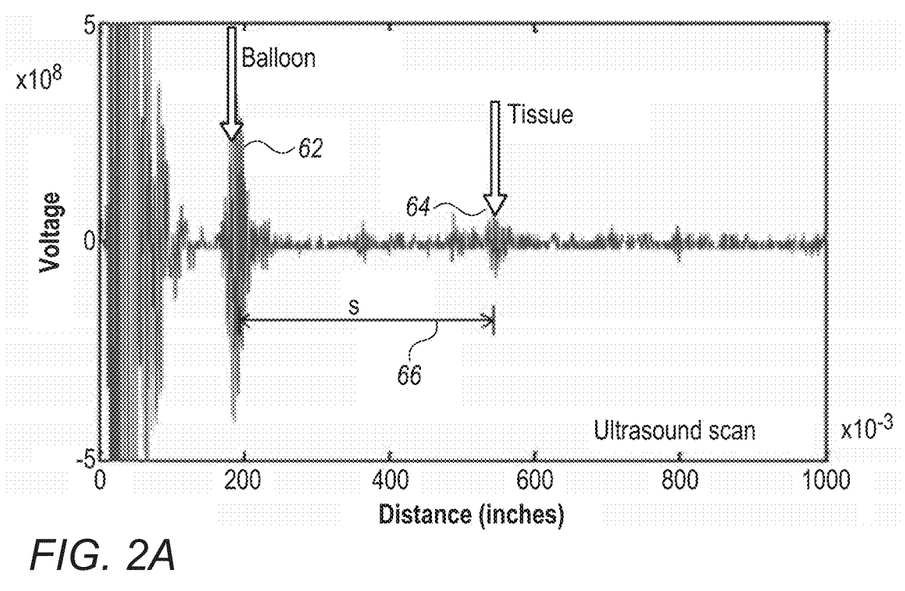
FIGS. 2A and 2B are graphs that exemplify echo-profiles produced by the ultrasound probe, in accordance with an embodiment of the present invention.
Figure 2B:
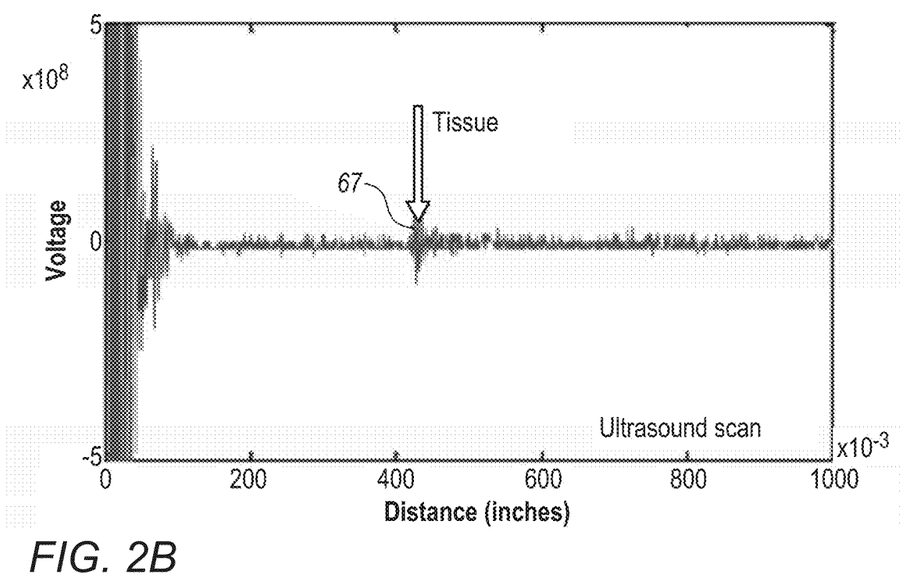

FIGS. 2A and 2B are graphs that exemplify one-dimensional echo-profiles produced by ultrasound probe 50, in accordance with an embodiment of the present invention. The one-dimensional echo-profiles are generated by ultrasound waves reflected from different directions, A and B, respectively, wherein the ultrasound waves were originally generated by two of ultrasound transducers 52 (seen in FIG. 3A). The figures show the one-dimensional echo-profiles after some analysis providing these in the form of voltage as a function of distance from the transducer.

In the present context, the term "echo profile" refers to any representation that is indicative of the amplitude of the reflected ultrasound wave as a function of distance from the transducer. Each echo profile is one-dimensional, is produced by a respective transducer 52, and pertains to a respective radial direction relative to the catheter axis.

As shown, the envelope of the echo-profile in FIG. 2A comprises two distinct features, a peak 62 centered about $200 \times 10^{-3}$ and a peak 64 centered around $550 \times 10^{-3}$ inches. These peaks were generated by reflections from the balloon wall and the surrounding anatomy surface. As marked on FIG. 2A, balloon 40 wall and surrounding anatomy surface are separated by a radial distance 's' 66 along a given direction A, which processor 41 may be configured to calculate. In the description hereinafter, distance 's' 66 is used generically to identify any set of one or more distances between balloon 40 wall and a surface of a surrounding anatomy.

FIG. 2B shows another echo-profile, wherein only a single peak 67 is seen, centered about $400 \times 10^{-3}$ inches. Peak 67 is associated with a single reflecting surface. This signal indicates that the balloon wall and the surrounding anatomy surface cannot be spatially differentiated along direction B, indicating contact.

FIGS. 3A and 3B are schematic, pictorial illustrations of a Radio Frequency (RF) inflatable balloon 40 wall in partial contact with ostium 54 of a pulmonary vein, in accordance with an embodiment of the present invention. The figures are also used hereinafter to visualize the type of data provided in FIGS. 2A and 2B. As seen, balloon 40 comprises RF ablation electrodes 51, wherein it is desired that part of each of electrodes 51 surfaces will contact ostium 54 prior to commencing an RF ablation treatment of ostium 54.

FIG. 3A provides a side view illustration of balloon 40 siting relative to ostium 54. Clearly, balloon 40 is not yet positioned optimally, e.g. with balloon 40 wall in full contact with ostium 54 over an entire balloon circumference, and hence shaft distal end 22 should be further advanced to meet that end. This situation is exemplified by the two signals shown in FIGS. 2A and 2B, received from different directions, A and B, respectively.

The one-dimensional echo profiles in the A and B directions provide physician 30 information on the quality of contact of ablation electrodes 51, through which the ultrasound waves propagate and are reflected. As seen, radial distance 's' 66 quantitatively provide a measure to the gap between the electrode disposed over balloon 40 wall along direction A and ostium 54. To enable the measurement of radial distances 's' 66 around an entire circumference of balloon 40, ultrasound probe 50 is located inside balloon 40, and comprises multiple ultrasound transducers that are distributed circumferentially within shaft distal end 22.

FIG. 3B provides a frontal illustration of a spatial relationship between balloon 40 and ostium 54. It further demonstrates, from another perspective, the partiality of the contact between balloon 40 wall and ostium 54, as demonstrated by the measurements along directions A and B, which FIGS. 2A and 2B exemplify. As illustrated in FIG. 3B, balloon 40 wall comprises numerous circumferences 44. The particular circumference along which full contact with surrounding anatomy will be achieved depends on that surrounding anatomy. As implied from FIG. 3B, a full understanding of the spatial relationship between balloon and ostium 54 requires multiple radial-distance measurements at multiple directions around entire circumference 44 of balloon 40.

In some embodiments, the radial directions of ultrasound transducers 52 are aligned with the positions of electrodes 51 on balloon 40. In other words, each transducer 52 is configured to transmit an ultrasound wave in the direction of a respective electrode 52, and to receive ultrasound reflections from that direction. The rationale behind this configuration is that contact quality is especially important at the electrodes, and often of lesser interest elsewhere. Nevertheless, in alternative embodiments, transducers 52 may be positioned at any other suitable positions relative to electrodes 52.

The example data in FIG. 2, and the pictorial illustrations in FIG. 3 the data refers to, are chosen purely for the sake of conceptual clarity. The disclosed techniques may similarly be applied using other system architecture. For example, ultrasound probe 50 may contain a varying number of transducers, depending on the required radial resolution. Ultrasound probe 50 may contain two or more rows of ultrasound transducers 52, which may generate nearly simultaneously or simultaneously two or more sets of measurements around multiple respective different entire circumferences 44 of balloon 40. In that case, directions A and B represent each an 'array A' and an 'array B' of directions along ostium 54 interface. Furthermore, processor 41 may generate a two-dimensional array of radial distances 's' 66 between balloon 40 wall and the surrounding anatomy surface over one or more entire circumferences 44 of the balloon. Processor 41 may further generate a graphical volumetric, such as a forward-looking map, to direct physician 30 how to further navigate balloon 40 into a balloon an optimized siting where full contact is achieved over an entire circumference 44 of balloon 40.

FIG. 4 is a schematic, pictorial illustration of a diagram of radial distances, displayed to physician 30 on monitor 27, in accordance with an embodiment of the present invention. Diagram 55 shows physician 30 multiple radial distances 's' 66 between balloon 40 wall and target surrounding ostium 54, over entire circumference 44 of balloon 40. Furthermore diagram 55 presents to physician 30 highlighted numerical values 68 of radial distances 's' 66.

The example configuration shown in FIG. 4 is chosen purely for the sake of conceptual clarity. There are numerous other ways that can be used for graphically and numerically presenting the distance information to physician 30. For example, two or more entire circumferences 44 and respective set of radial distances 's' 66 may be displayed in parallel on monitor 27 at any given time.

Figure 5:
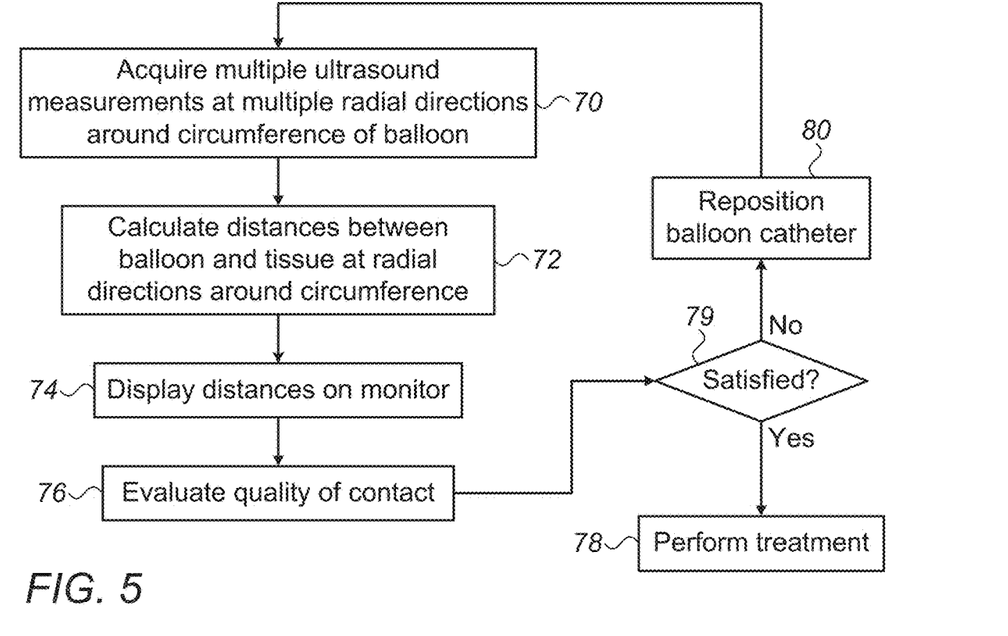
FIG. 5 is a flow chart that schematically illustrates a method for quantitatively estimating the extent of contact between a balloon wall and a surrounding anatomy, in accordance with an embodiment of the present invention.

FIG. 5 is a flow chart that schematically illustrates a method for quantitatively estimating the extent of contact between balloon 40 wall and a surrounding anatomy, in accordance with an embodiment of the present invention. The procedure commences with physician 30 initiating a measurement cycle to assess the quality of the balloon contact while he is positioning the balloon within a surrounding anatomy. The measurement cycles begin with acquiring multiple ultrasound measurements at multiple radial directions around the circumference of balloon. For that ultrasound transducers 52 generate multiple measurements along respective multiple radial directions that cover an entire circumference 44 of balloon 40, at a measurement step 70. Examples of such measurements are provided in FIG. 2.

At a calculation step 72, processor 41 calculates multiple respective radial distances 's' 66 between balloon 40 and the surface of the surrounding anatomy at radial directions around circumference 44, where respective measurement directions covering the entire circumference 44.

Monitor 27 displays diagram 55 of radial distances 's' 66 to physician 30, at a displaying step 74. After an evaluation step 76, physician 30 decides, at a decision step 79, if the quality of contact is satisfactory. If physician 30 concludes (at step 79) that the quality of contact is indeed satisfactory, then physician 30 commences with the planned medical procedure, such as an ablation treatment, at a treatment step 78. If physician 30 is dissatisfied with the quality of contact (at step 79), then he will reposition the balloon, at a realignment step 80. The procedure loops back to steps 70 and 72 and proceeds, until physician 30 completes the balloon contacting process.

The example flow chart shown in FIG. 5 is chosen purely for the sake of conceptual clarity. In alternative embodiments, the disclosed techniques may use any other suitable navigation and siting assisting schemes, comprising for example such that is based on presenting the physician a scale, for example, providing of a percentage or degree of the extent of contact between the balloon and the target anatomy, ranging from zero percent, wherein there is no contact between the balloon circumference and the anatomy to hundred percent (100%), wherein the entire balloon circumference is in contact with the anatomy. In an optional embodiment, monitor 27 may display visual guide or directions to physician 30 for further navigating balloon 40 into its optimal siting location within a target surrounding anatomy. In another optional embodiment, control console 24 may enable or disable RF power delivery to individual RF electrodes based upon an automatic determination of contact (i.e., enable RF power delivery only to electrodes found to be in contact with tissue).

Although the embodiments described herein mainly address cardiac treatments, the methods and systems described herein can also be used in other applications, such as in otolaryngology, neurology, sinuplasty, esophageal dilation and pulmonary angioplasty procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
a shaft for insertion into a body of a patient;
an inflatable balloon coupled to a distal end of the shaft, the inflatable balloon includes a plurality of ablation electrodes disposed on the inflatable balloon and is configured to perform a treatment to surrounding anatomy;
a radial array of ultrasound transducers, which are distributed circumferentially around the distal end of the shaft inside the balloon, and are configured to transmit ultrasound waves at respective radial directions and receive respective ultrasound reflections so that each of the respective radial directions corresponds directly to each of the plurality of ablation electrodes disposed on the inflatable balloon; and
a processor, configured to estimate and output to a user, based on the ultrasound reflections received from the ultrasound transducers, an extent of mechanical contact between the balloon and the surrounding anatomy.

2. The medical system according to claim 1, wherein each of the plurality of ablation electrode is configured to perform RF ablation.

3. The medical system according to claim 1, wherein the radial array of ultrasound transducers is configured to transmit the ultrasound waves at respective radial directions and receive the respective ultrasound reflections at the respective radial directions corresponding to the plurality of ablation electrodes disposed on the circumference of the inflatable balloon.

4. The medical system according to claim 1, wherein the processor is configured to calculate, based on the ultrasound reflections, respective radial distances between multiple locations on the inflatable balloon and multiple respective sites on a surface of the surrounding anatomy, and to estimate the extent of mechanical contact between the balloon and the surface of the surrounding anatomy based on the radial distances.

5. The medical system according to claim 4, wherein the processor is configured to calculate the radial distances by analyzing respective one-dimensional echo-profiles, comprising peaks indicative of the respective radial distances.

6. The medical system according to claim 5, wherein each of the ultrasound transducers is configured to produce a respective one-dimensional echo profile at a respective radial direction.

7. The medical system according to claim 5, wherein the processor is configured to analyze each echo profile along the respective radial direction independently of other echo profiles.

8. The medical system according to claim 4, wherein the processor is configured to present the radial distances graphically to the user.

9. The medical system according to claim 8, wherein the processor is configured to update the displayed radial distances at a given rate or by request.

10. A method, comprising:
inserting into a body of a patient an inflatable balloon coupled to a distal end of a shaft, the inflatable balloon includes a plurality of ablation electrodes disposed on the inflatable balloon for performing a treatment to surrounding anatomy;
using a radial array of ultrasound transducers, which are distributed circumferentially around the distal end of the shaft inside the balloon,
transmitting ultrasound waves at respective radial directions and receiving respective ultrasound reflections, the transmitting includes directing one or more of the ultrasound waves towards respective ablation electrodes disposed on the inflatable balloon; and
estimating and outputting to a user, based on the ultrasound reflections received from the ultrasound transducers, an extent of mechanical contact between the balloon and the surrounding anatomy.

11. The method according to claim 10, wherein performing the treatment comprises performing RF ablation.

12. The method according to claim 10, wherein transmitting the ultrasound waves comprises transmitting the ultrasound waves at respective radial directions and receiving the respective ultrasound reflections from the respective radial directions, covering an entire circumference of the inflatable balloon.

13. The method according to claim 10, wherein estimating the extent of mechanical contact comprises calculating radial distances between multiple locations on the inflatable balloon and multiple respective sites on a surface of the surrounding anatomy and estimating the extent of mechanical contact based on the calculated radial distances.

14. The method according to claim 13, wherein calculating the radial distances comprises analyzing respective one-dimensional echo-profiles, comprising peaks indicative of the respective radial distances.

15. The method according to claim 14, wherein analyzing the one-dimensional echo profiles comprises producing a one-dimensional echo profile by each of the ultrasound transducers at a respective radial direction.

16. The method according to claim 14, wherein analyzing the echo profiles comprises analyzing each echo profile independently of other echo profiles.

17. The method according to claim 13, wherein outputting the extent of mechanical contact comprises presenting the radial distances graphically to the user.

18. The method according to claim 17, wherein presenting the radial distances comprises updating the displayed radial distances at a given rate or by request.

* * * * *